US011357662B2

(12) United States Patent
Bruss (10) Patent No.: US 11,357,662 B2
(45) Date of Patent: Jun. 14, 2022

(54) MANDIBLE ADJUSTMENT APPARATUS

(71) Applicant: Ryan Bruss, Sherwood, OR (US)

(72) Inventor: Ryan Bruss, Sherwood, OR (US)

( * ) Notice: Subject to any disclaimer, the term of this patent is extended or adjusted under 35 U.S.C. 154(b) by 166 days.

(21) Appl. No.: 16/743,467

(22) Filed: Jan. 15, 2020

(65) Prior Publication Data

US 2020/0222228 A1  Jul. 16, 2020

Related U.S. Application Data

(60) Provisional application No. 62/792,586, filed on Jan. 15, 2019.

(51) Int. Cl.
*A61F 5/56* (2006.01)

(52) U.S. Cl.
CPC .................... *A61F 5/566* (2013.01)

(58) Field of Classification Search
CPC ...... A61F 5/56; A61F 5/566; A61F 2005/563; A61F 5/0006; A63B 71/085; A63B 71/086; A63B 71/088; A63B 71/081; A61C 7/06; A61C 7/08; A61C 7/36; A61C 7/12; A61C 7/125; A61C 7/14; A61C 7/141; A61C 7/143
USPC ........ 128/848, 859, 861, 862; 433/6, 18, 19, 433/24
See application file for complete search history.

(56) References Cited

U.S. PATENT DOCUMENTS

| | | | | |
|---|---|---|---|---|
| 5,499,633 A | * | 3/1996 | Fenton | A61F 5/566 128/848 |
| 6,055,986 A | * | 5/2000 | Meade | A61F 5/566 128/859 |
| 2011/0017220 A1 | * | 1/2011 | Lindsay | A61F 5/566 128/848 |
| 2014/0352704 A1 | * | 12/2014 | Farrell | A63B 71/085 128/862 |
| 2018/0078344 A1 | * | 3/2018 | Falkel | A61F 5/566 |
| 2018/0207021 A1 | * | 7/2018 | Newby | A61F 5/566 |
| 2020/0147473 A1 | * | 5/2020 | Maloney | B29C 51/266 |

* cited by examiner

*Primary Examiner* — Caitlin A Carreiro (74) *Attorney, Agent, or Firm* — Miller IP Law LLC (57) ABSTRACT

A method, system, apparatus, and/or device for adjusting a mandible of a user. The method, system, apparatus, and/or device may include: a top tray configured to be inserted into a mouth of a user to form around upper teeth of the user; a top position adjuster attached to a bottom portion of the top tray: a bottom tray configured to be inserted into the mouth of the user to form around lower teeth of the user; and a bottom position adjuster attached to a top portion of the bottom tray, where the top position adjuster and the bottom position adjuster are adjustable to move the top position adjuster or the bottom position adjuster laterally or longitudinally.

11 Claims, 10 Drawing Sheets

MANDIBLE ADJUSTMENT APPARATUS

CROSS-REFERENCES

This application claims priority to U.S. Provisional Patent Application No. 62/792,586 by Ryan Bruss for "Mandible Adjustment Apparatus," filed Jan. 15, 2019.

BACKGROUND

Obstructions or occlusions to an individual's airway may occur while the individual sleeps. For example, the palate and soft tissue around the individual's throat may cut off or restrict the flow of air to the individual's throat or the individual's tongue may fall backward towards his/her throat while he/she is sleeping and adversely affect the individual's ability to breath. A partial or complete blockage of the individual's airway may cause snoring, a reduction or lack of air supply to the individual respiratory system, choking, loss of sleep, heart disease, strokes, and so forth.

BRIEF DESCRIPTION OF THE DRAWINGS

The present description will be understood more fully from the detailed description given below and from the accompanying drawings of various implementations of the present embodiment, which is not to be taken to limit the present embodiment to the specific implementations but are for explanation and understanding.

DETAILED DESCRIPTION

The disclosed mandible adjustment apparatuses will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations. However, for the sake of brevity and clarity, each and every contemplated variation is not individually described in the following detailed description.

Throughout the following detailed description, a variety of mandible adjustment apparatus examples are provided. Related elements in the example embodiments may be identical, similar, or dissimilar in different examples. For the sake of brevity and clarity, related elements may not be redundantly explained in multiple examples. Instead, the use of same, similar, and/or related element names and/or reference characters may cue the reader that an element with a given name and/or associated reference character may be similar to another related element with the same, similar, and/or related element name and/or reference character in an example embodiment explained elsewhere herein. Elements specific to a given example may be described regarding that particular example embodiment. A person having ordinary skill in the art will understand that a given element need not be the same and/or similar to the specific portrayal of a related element in any given figure or example embodiment in order to share features of the related element.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding embodiments, elements, and/or features should be interpreted to be definite only regarding a specific embodiment and should not be interpreted as definite regarding the invention as a whole. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, and Abstract.

Where multiples of a particular element are shown in a figure, and where it is clear that the element is duplicated throughout the figure, only one label may be provided for the element, despite multiple instances of the element being present in the figure. Accordingly, other instances in the figure. of the element having identical or similar structure and/or function may not be redundantly labeled. A person having ordinary skill in the art will recognize based on the disclosure herein redundant and/or duplicated elements of the same figure. Despite this, redundant labeling may be included where helpful in clarifying the structure of the depicted example embodiments.

Obstructions or occlusions to an individual's airway while the individual sleeps may cut off or restrict the flow of air to the individual's airway and may cause snoring, a reduction or lack of air supply to the individual respiratory system, choking, loss of sleep, heart disease, strokes, and so forth. The obstructions and occlusions may be caused by the palate and/or tissue around the individual's throat cutting off or restricting the flow of air to the individual's throat. The obstructions and occlusions may be caused by the individual's tongue falling backward towards his/her throat.

Conventionally, to treat obstructions and occlusions to an individual's airway while he/she sleeps, the individual may use a continuous positive airway pressure (CPAP) machine that uses a hose and a mask or a nosepiece to deliver constant and steady air pressure to the individual's airway. Air is continuously blown down the patient's throat to maintain an open airway. The constant and steady air pressure may keep the individual's airway open while they sleep. Alternatively, surgery may be performed to remove tissue from the back of the individual's mouth, such as the uvula, tissue surrounding the uvula, and/or some or all of the individual's soft palate.

However, the hose and the mask of the CPAP machine may be strapped over an individual's nose and/or mouth, making the CPAP machine difficult and uncomfortable to use as the individual sleeps. The CPAP machine may also be relatively loud, making it difficult for the individual to sleep. Additionally, the CPAP machine may be large and difficult to travel with, making it difficult for the individual to travel with the CPAP machine. Furthermore, some individuals' bodies may not tolerate the positive airway pressure provided by the CPAP machine and may not be able to use the CPAP machine to keep their airway open as they sleep. Additionally, the cleaning regimen for the CPAP machine may be burdensome enough to be neglected, resulting in other breathing-related pathologies brought on by bacteria and/or fungus in the unclean CPAP machine. With regard to surgery, the surgery has inherent risks such as post-surgical hemorrhaging, poor healing of the surgical site, and/or infection, among others. Thus, the CPAP and/or surgery may not be acceptable remedies to treat airway obstructions and occlusions.

Implementations of the disclosure address the above-mentioned deficiencies and other deficiencies by providing methods, systems, devices, and/or apparatuses to keep an individual's mouth open and clear while the individual sleeps to maintain an open airway to the individual's throat. A mandible adjustment apparatus may include a top tray, a top position adjuster, a bottom tray, and a bottom position adjuster. In one embodiment, the top tray and the top position adjuster may be connected to form an upper mandible tray that may be inserted around upper teeth of an individual. In another embodiment, the bottom tray and the bottom position adjuster may be connected to form a lower mandible tray that may be inserted around lower teeth of the individual. The upper mandible tray and the lower mandible tray may be connected together in various defined configurations to form the mandible adjustment apparatus. The mandible adjustment apparatus may be inserted into the mouth of the individual to separate the individual's lower mandible from their upper mandible to keep the individual's airway open and clear.

Figure 1:
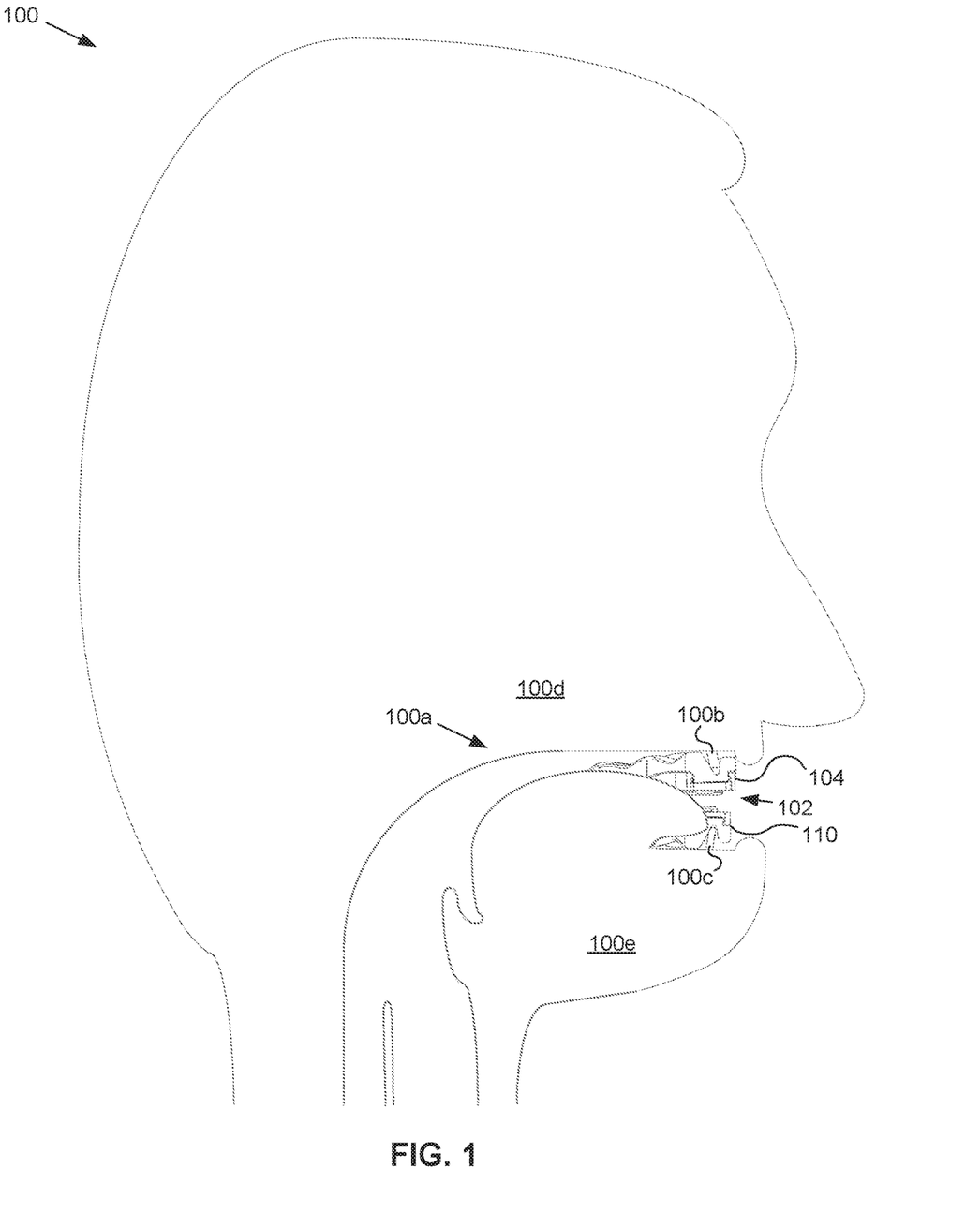
FIG. 1 illustrates an individual with a mandible adjustment apparatus in his/her mouth, according to an embodiment.

FIG. 1 illustrates an individual 100 with a mandible adjustment apparatus 102 in his/her mouth 100a, according to an embodiment. The mandible adjustment apparatus 102 may be configured to be inserted into the mouth 100a of the individual 100 to keep the individual's mouth 100a open and clear while the individual sleeps. The mandible adjustment apparatus 102 may include an upper mandible tray 104 and a lower mandible tray 110. The upper mandible tray 104 may be configured to fit around or conform to upper teeth 100b of the individual 100 and the lower mandible tray 110 may be configured to fit around or conform to lower teeth 100c of the individual 100 to separate the upper teeth 100b from the lower teeth 100c. The upper teeth 100b may include an upper bicuspid of the individual 100 and/or an upper molar of the individual 100. The lower teeth 100c may include a lower bicuspid of the individual 100 and/or a lower molar of the individual 100.

The mouth 100a of the individual 100 may be formed by an upper mandible 100d and a lower mandible 100e. During sleep, the lower mandible 100e my relax into a relaxed position which may cause obstruction of the individual's mouth 100a by, for example, a tongue of the individual pressing against a soft palate of the individual. The mandible adjustment apparatus 102 may maintain a position of the lower mandible 100e during sleep that prevents the lower mandible 100e from relaxing such that the mouth 100a becomes obstructed. Different individuals may have different relaxed positions of the lower mandible 100e. Over time, the relaxed position of the lower mandible 100e of the individual 100 may change. Accordingly, the mandible adjustment apparatus 102 may be adjusted to maintain the lower mandible 100e in different positions for different individuals or to maintain the lower mandible 100e in a different position for the individual 100 as the relaxed position of the lower mandible 100e changes.

Figure 2:
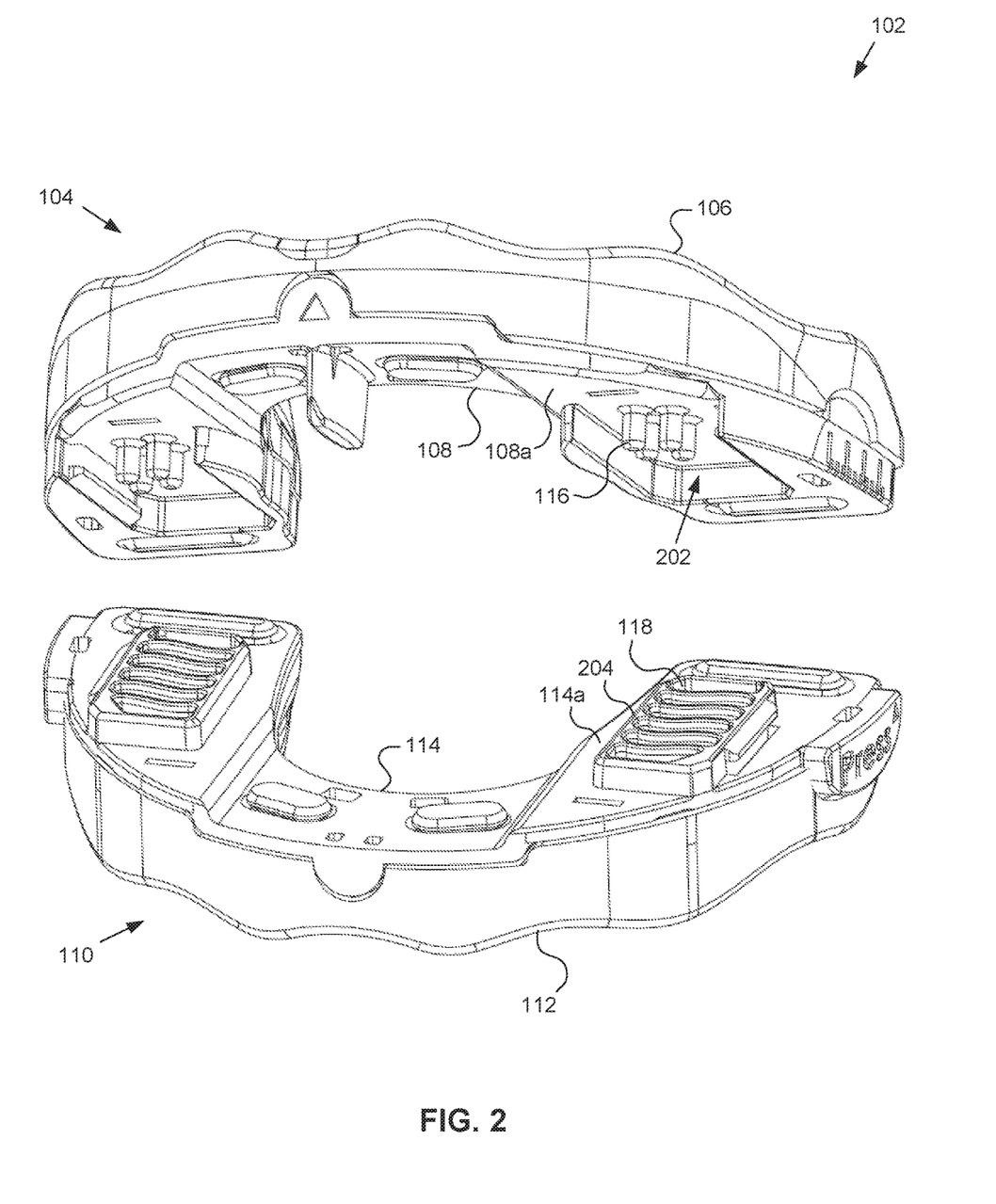
FIG. 2 illustrates a mandible adjustment apparatus with an upper mandible tray separated from a lower mandible tray, according to an embodiment.

FIG. 2 illustrates the mandible adjustment apparatus 102 with the upper mandible tray 104 separated from the lower mandible tray 110, according to an embodiment. Some of the features in FIG. 2 are the same or similar to some of the features in FIG. 1 as noted by the same reference numbers, unless expressly described otherwise. Additionally, reference may be made to features shown in FIG. 1 and not shown in FIG. 2. In one embodiment, the upper mandible tray 104 may include a top tray 106 and a top position adjuster 108 that may be configured to connect together to form the upper mandible tray 104 that may be inserted around the upper teeth 100b of the individual 100. In one example, the top tray 106 may be a flexible cover with a top portion that includes a teeth channel that forms around the upper teeth of the individual to secure the upper mandible tray 104 to the upper teeth of the individual. In one example, the teeth channel of the top tray 106 may be a flexible rubber or plastic material that may be formed or molded to a shape corresponding to the upper teeth 100b of the individual 100. For example, the top tray 106 may be heated and pressed against the upper teeth 100b of the individual 100 such that the shape of the top tray 106 corresponds to the shape of the upper teeth 100b. The bottom portion of the top tray 106 may include fasteners to connect the bottom portion of the top tray 106 to a top portion of the top position adjuster 108. The fasteners may include pegs, pins, dowels, hooks, hangers, and so forth that may be inserted into openings in the top position adjuster 108 to connect the top tray 106 to the top position adjuster 108.

In another embodiment, the lower mandible tray 110 may include a bottom tray 112 and a bottom position adjuster 114 that may be configured to connect together to form the lower mandible tray 110 that may be inserted around the lower teeth 100c of the individual 100. In one example, the bottom tray 112 may be a flexible cover with a bottom portion that includes a teeth channel that forms around the lower teeth 100c of the individual 100 to secure the lower mandible tray 110 to the lower teeth of the individual. In one example, the teeth channel of the bottom tray 112 may be a flexible rubber or plastic material that may be formed or molded to a shape corresponding to the lower teeth 100c of the individual 100. For example, the bottom tray 112 may be heated and pressed against the lower teeth 100c of the individual 100 such that the shape of the bottom tray 112 conforms to the shape of the lower teeth 100c. The upper portion of the bottom tray 112 may include fasteners to connect the upper portion of the bottom tray 112 to a bottom portion of the bottom position adjuster 114. The fasteners may include pegs, pins, dowels, hooks, hangers, and so forth that may be inserted into cavities or openings in the bottom position adjuster 114 to connect the bottom tray 112 to the bottom position adjuster 114.

The top position adjuster 108 may be configured to connect with the bottom position adjuster 114 so that the mandible adjustment apparatus 102 is a single device or apparatus that may be inserted into the mouth 100a of the individual 100. In one embodiment, the top position adjuster 108 may include one or more protuberances 116 that may extend downward from a bottom surface 108a of the top position adjuster 108. In one example, the bottom surface 108a of the top position adjuster 108 may include an indent or a recess 202 in which the protuberances 116 may be located. The recess 202 and/or the protuberances 116 may be positioned on the top position adjuster 108 to be directly under one or more of the upper teeth 100b of the individual 100 as the individual 100 wears the upper mandible tray 104. The bottom position adjuster 114 may include one or more cavities or channels 118 that may be located along a top surface 114a of the bottom position adjuster 114. In another example, the cavities or channels 118 may be formed in a raised portion 204 of the bottom position adjuster 114 that extends upward from the top surface 114a of the bottom position adjuster 114. The channels 118 may be positioned on the bottom position adjuster 114 to be directly over one or more of the lower teeth 100c of the individual 100 as the individual 100 wears the lower mandible tray 110. The channels 118 may be aligned perpendicular to a row of the lower teeth 100c of the individual 100. For example, the channels 118 may be aligned perpendicular to a row of molars of the individual 100.

The protuberances 116 may be male-type fasteners that are configured to mate with the channels 118. The channels 118 may be female-type fasteners. For example, the protuberances 116 and the channels 118 may be located on corresponding surfaces of the top position adjuster 108 and the bottom position adjuster 114 to connect the top position adjuster 108 with the bottom position adjuster 114. The protuberances 116 may be inserted into one or more of the channels 118. In one embodiment, the bottom position adjuster 114 may include multiple channels 118 that may be configured to receive the protuberances 116. The multiple channels 118 may allow the individual 100 to adjust the upper mandible tray 104 relative to the lower mandible tray 110 by inserting the protuberances 116 into different channels 118 or within different portions of the same channels 118. In one example, the upper mandible tray 104 may be adjusted longitudinally (i.e. backward and forward) relative to the lower mandible tray 110 by inserting the protuberances 116 into different channels 118. In another example, the upper mandible tray 104 may be adjusted laterally (i.e. right to left) relative to the lower mandible tray 110 by inserting the protuberances 116 different portions of the same channels 118.

The adjustability of the upper mandible tray 104 relative to the lower mandible tray 110 may allow a user to position each of the upper mandible tray 104 and the lower mandible tray 110 at optimal positions such that the upper mandible tray 104 and the lower mandible tray 110 are comfortable when the mandible adjustment apparatus 102 is positioned within the mouth 100a of the individual 100. For example, when the upper teeth 100b of the individual 100 extend farther forward than the lower teeth 100c, the mandible adjustment apparatus 102 may be configured to fit the mouth 100a of the individual 100. In another example, when the upper teeth 100b of the individual 100 extend farther to the left or right of the lower teeth 100c, the mandible adjustment apparatus 102 may be configured to fit the mouth 100a of the individual 100.

Figure 3A:
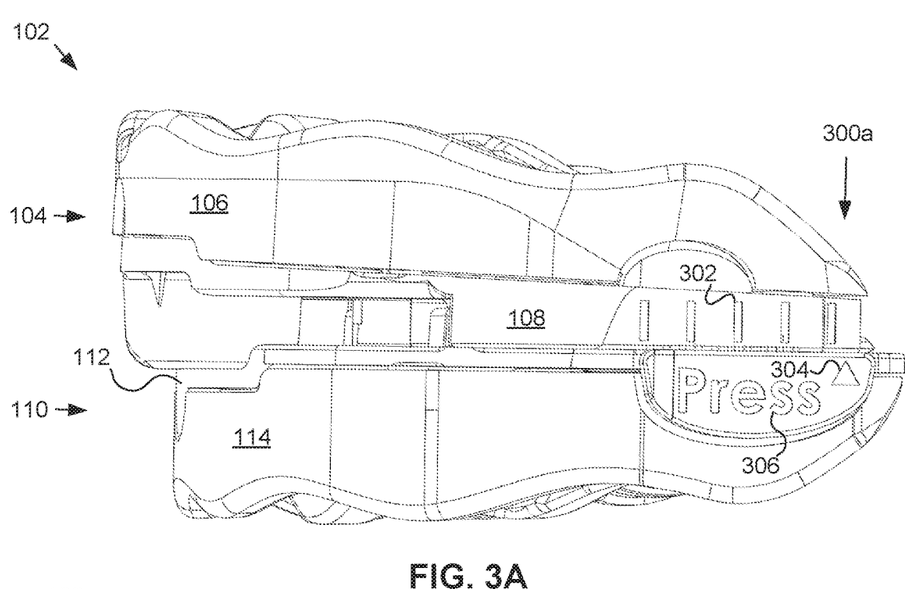
FIG. 3A illustrates a side view of a mandible adjustment apparatus in a first longitudinal position, according to an embodiment.

FIG. 3A illustrates a side view of the mandible adjustment apparatus 102 in a first longitudinal position 300a, according to an embodiment. Some of the features in FIG. 3A are the same or similar to some of the features in FIGS. 1-2 as noted by the same reference numbers, unless expressly described otherwise. Additionally, reference may be made to features shown in any of FIGS. 1-2 and not shown in FIG. 3A. The upper mandible tray 104 may include a set of alignment marks 302. The lower mandible tray 110 may include an alignment indicator 304. The lower mandible tray 110 may also include an orientation indicator 306. A position of the alignment indicator 304 relative to the alignment marks 302 may indicate a configuration of a bite of the individual 100. The alignment marks 302 may indicate an alignment interval of the upper mandible tray 104 relative to the lower mandible tray 110. For example, the individual may have a horizontal overbite. Alignment of the alignment indicator 304 with a rearward alignment mark may indicate the individual has the horizontal overbite. The relative position of the alignment indicator 304 relative to the alignment marks 302, i.e. the alignment interval, may indicate a degree of the overbite.

In one embodiment, the alignment marks 302 and the alignment indicator 304 may allow the individual 100 to reassemble the mandible adjustment apparatus 102 to an optimal alignment for the individual 100. For example, the mandible adjustment apparatus 102 may be disassembled to be cleaned. The upper mandible tray 104 may be separated from the lower mandible tray 110. The top tray 106 may be separated from the top position adjuster 108. The bottom tray 112 may be separated from the bottom position adjuster 114. The separated pieces of the mandible adjustment apparatus 102 may be cleaned and then reassembled. The individual 100 may use the alignment marks 302 and the alignment indicator 304 to align the upper mandible tray 104 with the lower mandible tray 110 as the upper mandible tray 104 and the lower mandible tray 110 are reconnected.

In various embodiments, the alignment marks 302 may be on the upper mandible tray 104 and/or the lower mandible tray 110. The alignment marks 302 may be on the top tray 106 and/or the top position adjuster 108. The alignment marks 302 may be on the bottom tray 112 and/or on the bottom position adjuster 114. The alignment indicator 304 may be on the upper mandible tray 104 and/or the lower mandible tray 110. The alignment indicator 304 may be on the top tray 106 and/or the top position adjuster 108. The alignment indicator 304 may be on the bottom tray 112 and/or the bottom position adjuster 114. In various embodiments, the mandible adjustment apparatus 102 may include corresponding alignment marks 302 on the upper mandible tray 104 and on the lower mandible tray 110. In various embodiments, the mandible adjustment apparatus 102 may include corresponding alignment indicators 304 on the upper mandible tray 104 and on the lower mandible tray 110.

The orientation indicator 306 may indicate to the individual a correct orientation of the mandible adjustment apparatus 102 for inserting into the mouth 100a of the individual 100. The orientation indicator 306 may indicate to the individual 100 the correct orientation by placement on one of the mandible trays. For example, placement of the orientation indicator 306 on the lower mandible tray 110 may indicate to the individual 100 which of the mandible trays is the lower mandible tray 110, and that the mandible tray with the orientation indicator 306 corresponds to the lower teeth 100c of the individual 100. Placement of the orientation indicator 306 on the upper mandible tray 104 may indicate to the individual that the mandible tray with the orientation indicator 306 corresponds to the upper teeth 100b of the individual 100. In one embodiment, the orientation indicator 306 may include one or more letters and/or words. The orientation of the letters and/or words may indicate to the individual 100 a correct orientation of the mandible adjustment apparatus 102 in the mouth 100a of the individual 100.

Figure 3B:
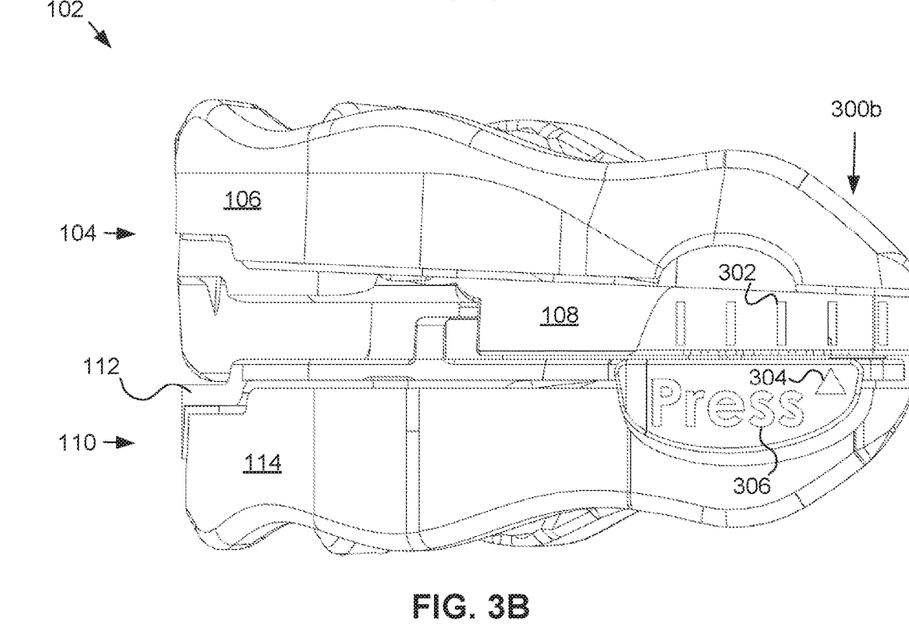
FIG. 3B illustrates a side view of the mandible adjustment apparatus in a second longitudinal position, according to an embodiment.

FIG. 3B illustrates a side view of the mandible adjustment apparatus 102 in a second longitudinal position 300b, according to an embodiment. Some of the features in FIG. 3B are the same or similar to some of the features in FIGS. 1-3A as noted by the same reference numbers, unless expressly described otherwise. Additionally, reference may be made to features shown in any of FIGS. 1-3A and not shown in FIG. 3B. As indicated by a relative position of the alignment indicator 304 relative to the alignment marks 302, the second longitudinal position 300b is different from the first longitudinal position 300a. The first longitudinal position 300a in FIG. 3A may correspond to the individual 100 having an overbite. The second longitudinal position 300b may correspond to the individual 100 having a normal bite. Accordingly, the mandible adjustment apparatus 102 may allow the individual 100 to track the progress of treatment for an overbite or an underbite.

Figure 3C:
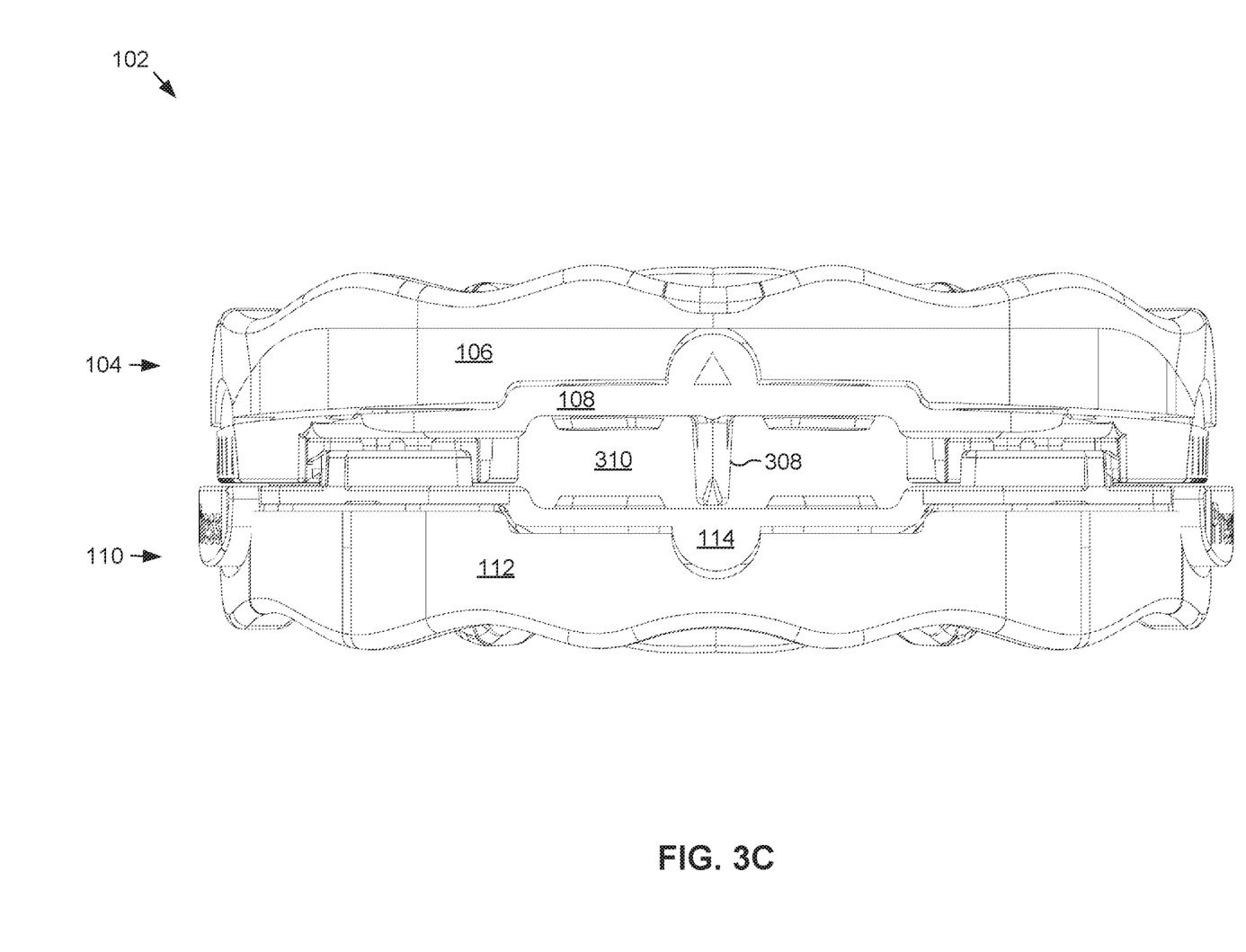
FIG. 3C illustrates a head-on view of the mandible adjustment apparatus, according to an embodiment.

FIG. 3C illustrates a head-on view of the mandible adjustment apparatus 102, according to an embodiment. Some of the features in FIG. 3C are the same or similar to some of the features in FIGS. 1-3B as noted by the same reference numbers, unless expressly described otherwise. Additionally, reference may be made to features shown in any of FIGS. 1-3B and not shown in FIG. 3C. The mandible adjustment apparatus 102 may include a spacer tab 308. The spacer tab 308 may be positioned between incisors of the individual 100 as the mandible adjustment apparatus 102 is worn by the individual 100 in the mouth 100a of the individual 100. The spacer tab 308 may maintain an open airway 310 between the upper mandible tray 104 and the lower mandible tray 110. The spacer tab 308 may prevent the individual 100 from closing the airway 310, such as by biting and/or grinding the individual's teeth during sleep. The spacer tab 308 may, in an embodiment, be integrated with and extend from the top position adjuster 108. The spacer tab 308 may, in another embodiment, be integrated with and extend from the bottom position adjuster 114. The spacer tab 308 may be aerodynamic, such as by having a rounded surface, to minimize drag and turbulence within the mouth 100a of the individual 100 as the individual 100 breathes. This may enhance a comfort of the mandible adjustment apparatus 102 relative to other embodiments where the spacer tab 308 is not aerodynamically-shaped.

In another embodiment, the airway 310 may extend from a front of the mandible adjustment apparatus 102 to a back of the mandible adjustment apparatus 102. A center portion of the top tray 106 and the top position adjuster 108 may curve or extend upward relative to the bottom tray 112 and the bottom position adjuster 114 to provide the airway 310. In another example, a center portion of the bottom tray 112 and the bottom position adjuster 114 may curve or extend downward relative to the top tray 106 and the top position adjuster 108 to provide the airway 310. In another example, a center portion of the top tray 106 and the top position adjuster 108 may curve or extend upward relative to the bottom tray 112 and the bottom position adjuster 114 and a center portion of the bottom tray 112 and the bottom position adjuster 114 may curve or extend downward relative to the top tray 106 and the top position adjuster 108 to provide the airway 310. The airway 310 may be a cutout pattern in the center of the mandible adjustment apparatus 102 to provide a secure fit in the mouth of the user while providing a relatively large breathing space for the user.

Figure 4A:
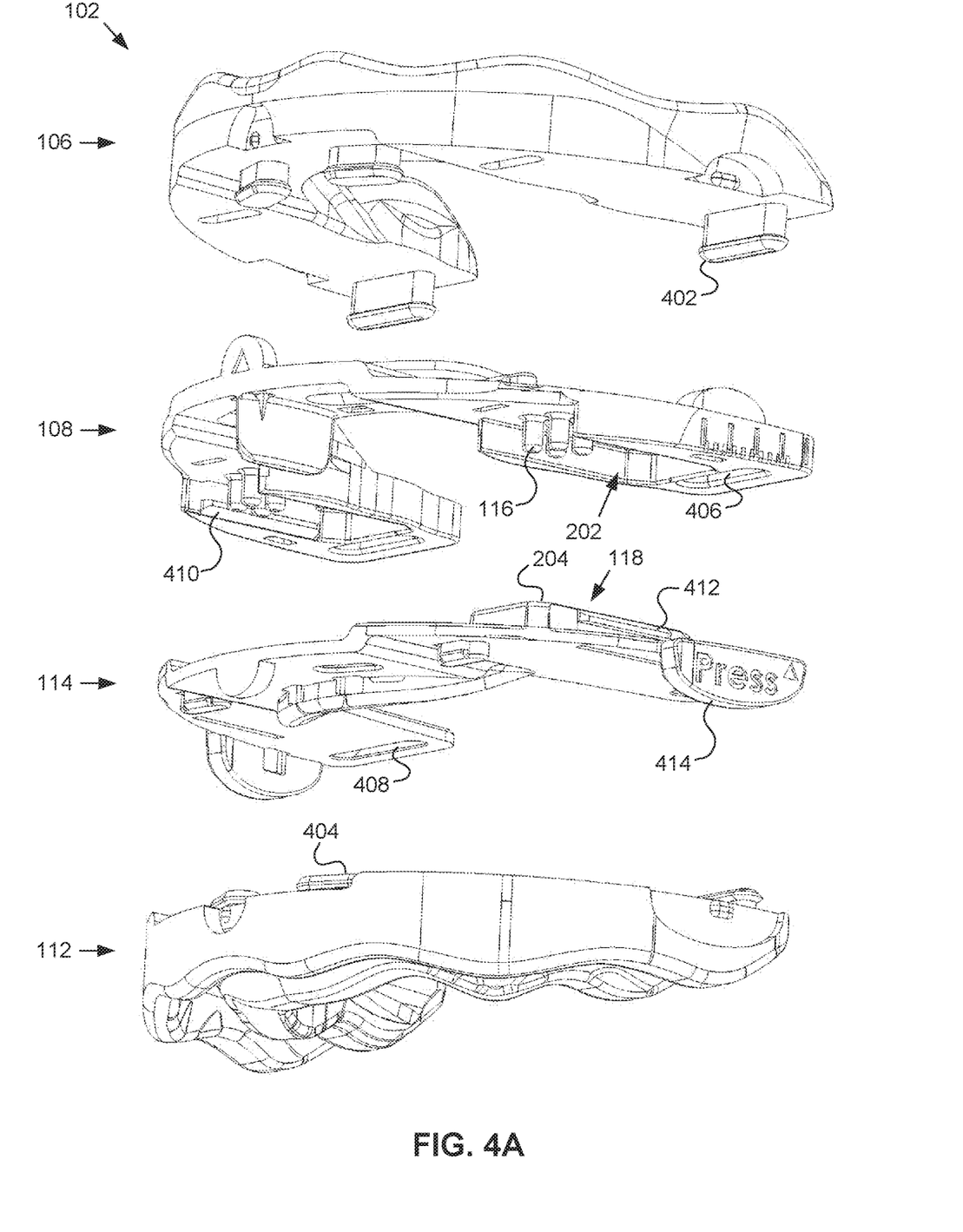
FIG. 4A illustrates a bottom perspective exploded view of the mandible adjustment apparatus, according to an embodiment.

FIG. 4A illustrates a bottom perspective exploded view of the mandible adjustment apparatus 102, according to an embodiment. Some of the features in FIG. 4A are the same or similar to some of the features in FIGS. 1-3C as noted by the same reference numbers, unless expressly described otherwise. Additionally, reference may be made to features shown in any of FIGS. 1-3C and not shown in FIG. 4A. As discussed above, the mandible adjustment apparatus 102 may include the top tray 106, the top position adjuster 108, the bottom tray 112, and the bottom position adjuster 114. A first set of male fasteners 402 may extend from the top tray 106. A second set of male fasteners 404 may extend from the bottom tray 112. A first set of female fasteners 406 may be formed in the top position adjuster 108. A second set of female fasteners 408 may be formed in the bottom position adjuster 114.

The first set of male fasteners 402 may insert into the first set of female fasteners 406 to join the top tray 106 to the top position adjuster 108. The first set of fastener sides, i.e. the first set of male fasteners 402 and the first set of female fasteners 406, may include a hook-and-catch snap joint. The second set of male fasteners 404 may insert into the second set of female fasteners 408 to join the bottom tray 112 to the bottom position adjuster 114. The second set of fastener sides, i.e. the second set of male fasteners 404 and the second set of female fasteners 408, may include a hook-and-catch snap joint. In an embodiment, the female fasteners may include openings and the male fasteners may include protrusions with hooks or catches. The male fasteners may be compressible to press through the openings, and the hooks or catches may catch against edges of the opening to prevent the male fasteners from pulling through the openings The female fasteners may be stretchable to stretch as the male fasteners press through the openings. In one embodiment, the first set of male fasteners 402 may extend from the top position adjuster 108 and the first set of female fasteners 406 may be formed in the top tray 106. In another embodiment, the second set of male fasteners 404 may extend from the bottom position adjuster 114 and the second set of female fasteners 408 may be formed in the bottom tray 112.

The top position adjuster 108 may include the recess 202 in which the protuberances 116 may be disposed. The recess 202 may include a catch 410. The bottom position adjuster 114 may include the raised portion 204 in which the channels 118 may be disposed. The raised portion 204 may include a hook 412. Together, the recess 202 and the raised portion 204 may form a snap joint. As the upper mandible tray 104 is brought together with the lower mandible tray 110, the raised portion 204 may insert into the recess 202. As the raised portion 204 inserts into the recess 202, the protuberances 116 may insert into the channels 118. The hook 412 may snap over the catch 410, securing the upper mandible tray 104 to the lower mandible tray 110. The bottom position adjuster 114 may include a pressing surface 414. In an embodiment, the bottom position adjuster 114 may include two pressing surfaces 414 positioned opposite each other on the bottom position adjuster 114. Pressure on the pressing surfaces 414 may deflect the hook 412 away from the catch 410 and release the raised portion 204 from the recess 202. Accordingly, pressure on the pressing surface 414 may release the upper mandible tray 104 from the lower mandible tray 110.

In various embodiments, the elements described above may be arranged differently. For example, the raised portion 204 may be on the top position adjuster 108 and the recess 202 may be formed in the bottom position adjuster 114. The pressing surface 414 may be formed on the top position adjuster 108. The hook 412 may be disposed on the protuberances 116 and the catch 410 may be disposed in the channels 118. Accordingly, the protuberances 116 and the channels 118 may form a hook-and-catch snap joint.

The top tray 106, the top position adjuster 108, the bottom tray 112, and/or the bottom position adjuster 114 may be formed of a plastic material such as a thermoplastic, an injection-molded plastic, and so forth. The top tray 106 may be of unibody construction, and/or the bottom tray 112 may be of unibody construction. The top position adjuster 108 may be of unibody construction, and/or the bottom position adjuster 114 may be of unibody construction. The top tray 106 and the bottom tray 112 may be formed of the same material, and the top position adjuster 108 and the bottom position adjuster 114 may be formed of the same material as each other but a different material than the top tray 106 and the bottom tray 112. The top tray 106 and/or the bottom tray 112 may be configured to fit around or conform to two or more of the upper teeth 100*b* and/or the lower teeth 100*c*, respectively. The top tray 106, the top position adjuster 108, the bottom tray 112, and/or the bottom position adjuster 114 may be horseshoe-shaped. Accordingly, the top position adjuster 108 may extend around the mouth 100*a* of the individual 100 from top right-side molars to top left-side molars of the individual 100. Similarly, the bottom position adjuster 114 may extend around the mouth 100*a* of the individual 100 from bottom right-side molars to bottom left-side molars of the individual 100. The top position adjuster 108 may include a right-side set of protuberances 116 and a left-side set of protuberances 116. The bottom position adjuster 114 may include a right-side set of channels 118 and a left-side set of channels 118.

Figure 4B:
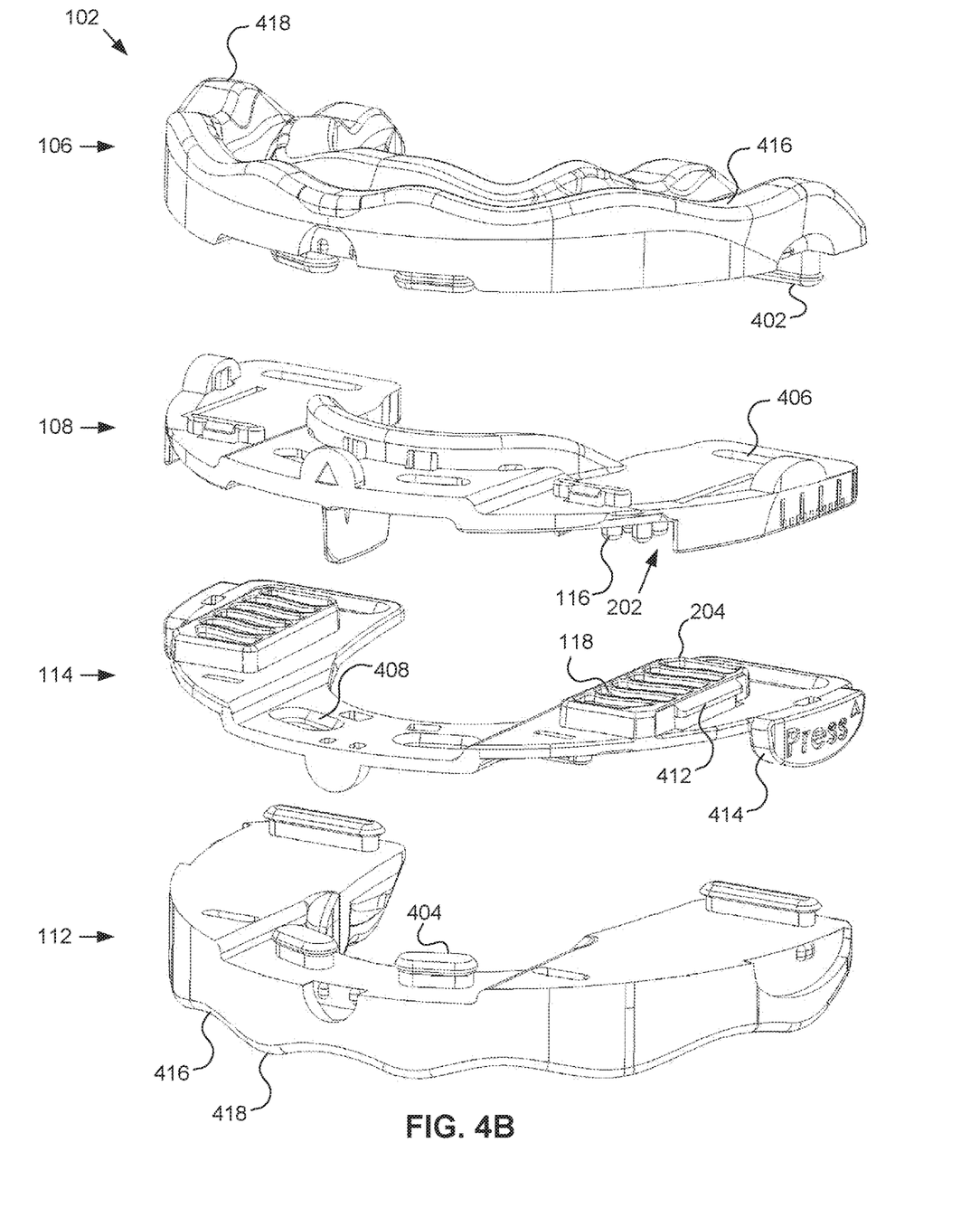
FIG. 4B illustrates a top perspective exploded view of the mandible adjustment apparatus, according to an embodiment.

FIG. 4B illustrates a top perspective exploded view of the mandible adjustment apparatus 102, according to an embodiment. Some of the features in FIG. 4B are the same or similar to some of the features in FIGS. 1-4A as noted by the same reference numbers, unless expressly described otherwise. Additionally, reference may be made to features shown in any of FIGS. 1-4A and not shown in FIG. 4B. From the top perspective, the channels 118 in the raised portion 204 are visible.

In one embodiment, the top tray 106 and/or the bottom tray 112 may have a wave pattern. The wave pattern may enable the top tray 106 and/or the bottom tray 112 to better fit around the upper teeth 100*b* and gums or lower teeth 100*c* and gums, respectively, of the individual 100 by reducing the overall volume of the mandible adjustment apparatus 102. For example, valleys 416 or bottom portions of the wave pattern of the top tray 106 and/or the bottom tray 112 may provide an area of space for the gums of the individual to spread out to or breathe while the crests 418 or top portions of the wave pattern may secure the top tray 106 and/or the bottom tray 112 to the teeth of the individual. The number of valleys 416 and crests 418 in the wave patterns are not intended to be limiting and may be increased or decreased based on the size of the user's mouth, the sensitivity of the user's teeth or gums, and so forth.

Figure 5A:
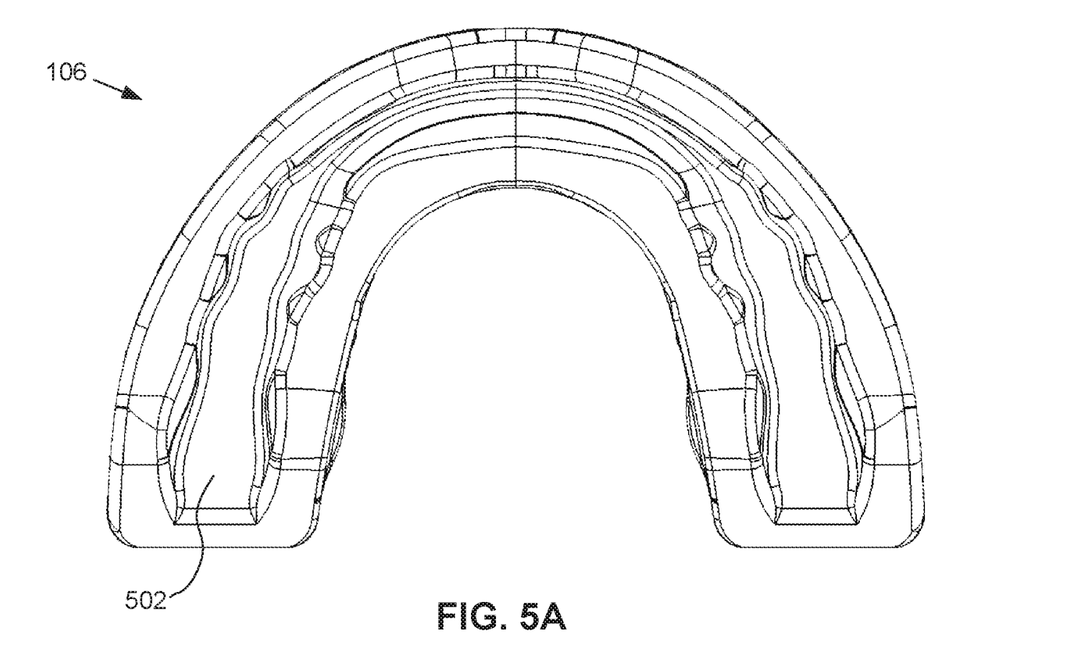
FIG. 5A illustrates a top view of a top tray of a mandible adjustment apparatus, according to an embodiment.

FIG. 5A illustrates a top view of the top tray 106, according to an embodiment. Some of the features in FIG. 5A are the same or similar to some of the features in FIGS. 1-4B as noted by the same reference numbers, unless expressly described otherwise. Additionally, reference may be made to features shown in any of FIGS. 1-4B and not shown in FIG. 5A. The top tray 106 may include an upper teeth channel 502. The upper teeth channel 502 may be configured to receive one or more upper teeth of the individual, such as the upper teeth 100*b*.

The top tray 106 may be formed of a remoldable polymer that softens when heated above a temperature, such as above 110° F. In an embodiment, the remoldable polymer may retain shape at temperatures up to 110° F., 120° F., 130° F., or 140° F. In an embodiment, the remoldable polymer may soften at temperatures between 110° F. and 200° F., between 120° F. and 200° F., between 130° F. and 200° F., or between 140° F. and 200° F. The top tray 106 may be remoldable to allow the upper teeth channel 502 to conform around the upper teeth 100*b* of the individual 100. For example, the top tray 106 may be heated to soften the top tray 106, and the individual 100 may insert the top tray in the individual's mouth 100*a* around the upper teeth 100*b* of the individual. The upper teeth channel 502 may conform to a shape of the upper teeth 100*b*. As the top tray 106 cools, the upper teeth channel 502 may retain the shape of the upper teeth 100*b*.

The top position adjuster 108 may be formed of a rigid polymer having a higher hardness and/or thermal resistance than the top tray 106. For example, whereas the top tray 106 may soften at temperatures ranging from 110° F. to 200° F., the top position adjuster 108 may remain rigid at temperatures ranging from 110° F. to 200° F. In an embodiment, the remoldable polymer may include ethylene-vinyl acetate. In an embodiment, the rigid polymer may be formed of polyurethane plastic. The top tray 106 may be softer than the top position adjuster to form a compressible barrier between the upper teeth 100*b* and the top position adjuster 108. The top position adjuster 108 may be rigid to hold open the mouth 100*a* of the individual 100 and to affix the upper mandible tray 104 to the lower mandible tray 110.

Figure 5B:
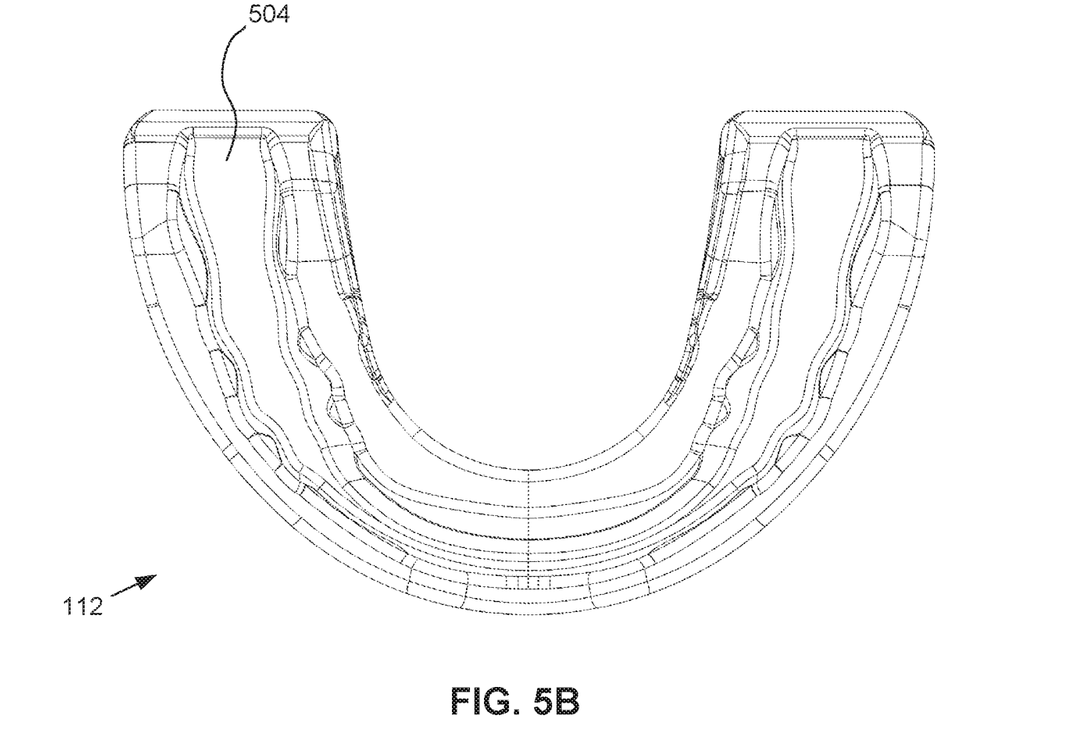
FIG. 5B illustrates a bottom view of a bottom tray of the mandible adjustment apparatus, according to an embodiment.

FIG. 5B illustrates a bottom view of the bottom tray 112, according to an embodiment. Some of the features in FIG. 5B are the same or similar to some of the features in FIGS. 1-5A as noted by the same reference numbers, unless expressly described otherwise. Additionally, reference may be made to features shown in any of FIGS. 1-5A and not shown in FIG. 5B. The bottom tray 112 may include a lower teeth channel 504. The lower teeth channel 504 may be configured to receive one or more lower teeth of the individual 100, such as the lower teeth 100*c*.

The bottom tray 112 may be formed of the remoldable polymer that softens when heated. In an embodiment, the remoldable polymer may retain shape at temperatures up to 110° F., 120° F., 130° F., or 140° F. In an embodiment, the remoldable polymer may soften at temperatures between 110° F. and 200° F., between 120° F. and 200° F., between 130° F. and 200° F., or between 140° F. and 200° F. The bottom tray 112 may be remoldable to allow the lower teeth channel 504 to conform around the lower teeth 100*c* of the individual 100. For example, the bottom tray 112 may be heated to soften the bottom tray 112, and the individual 100 may insert the top tray in the individual's mouth 100*a* around the lower teeth 100*c* of the individual 100. The lower teeth channel 504 may conform to a shape of the lower teeth 100c. As the bottom tray 112 cools, the lower teeth channel 504 may retain the shape of the lower teeth 100c.

The bottom position adjuster 114 may be formed of a rigid polymer having a higher hardness and thermal resistance than the bottom tray 112. For example, whereas the bottom tray 112 may soften at temperatures ranging from 110° F. to 200° F., the bottom position adjuster 114 may remain rigid at temperatures ranging from 110° F. to 200° F. In an embodiment, the remoldable polymer may include ethylene-vinyl acetate. In an embodiment, the rigid polymer may be formed of polyurethane plastic. The bottom tray 112 may be softer than the bottom position adjuster 114 to form a compressible barrier between the lower teeth 100c and the bottom position adjuster 114. The bottom position adjuster 114 may be rigid to hold open the mouth 100a of the individual 100 and to affix the lower mandible tray 110 to the upper mandible tray 104.

Figure 6A:
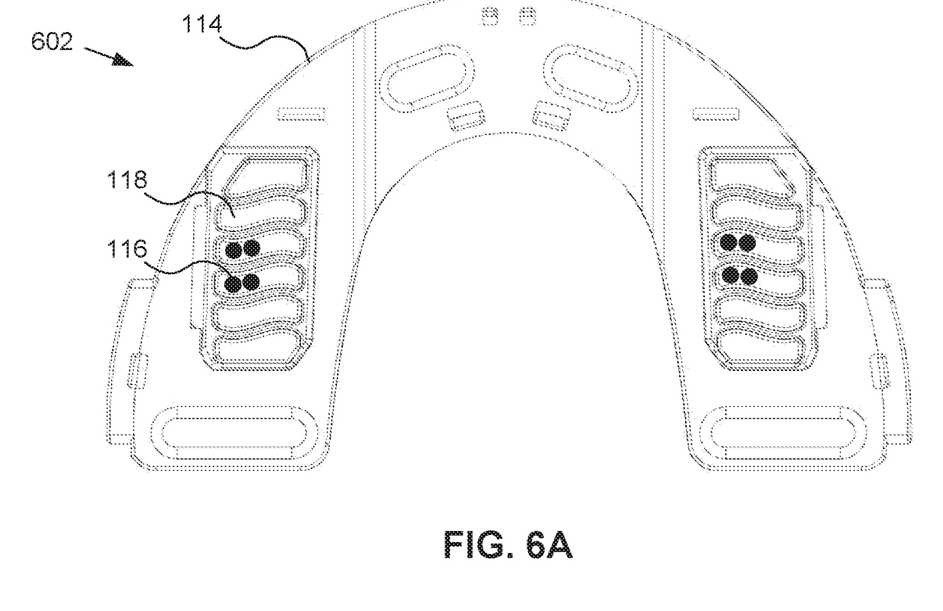
FIG. 6A illustrates a top view of a bottom position adjuster in a first lateral position, according to an embodiment.

FIG. 6A illustrates a top view of the bottom position adjuster 114 in a first lateral position 602, according to an embodiment. Some of the features in FIG. 6A are the same or similar to some of the features in FIGS. 1-5B as noted by the same reference numbers, unless expressly described otherwise. Additionally, reference may be made to features shown in any of FIGS. 1-5B and not shown in FIG. 6A. The first lateral position 602 of the top position adjuster 108 relative to the bottom position adjuster 114 is reflected in the relative position of the protuberances 116 in the channels 118. The top position adjuster 108 may be shifted left relative to the bottom position adjuster 114. The protuberances 116 may shift in the channels 118, which may allow the lower mandible 100e of the individual 100 to shift side to side. The protuberances 116 may hook into the channels 118 to secure the top position adjuster 108 to the bottom position adjuster 114.

Figure 6B:
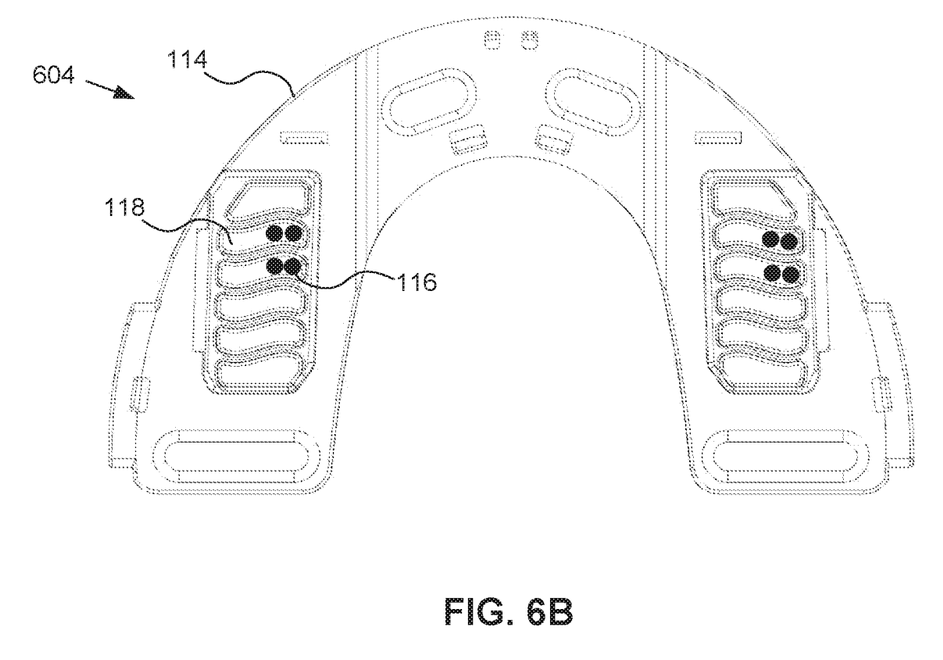
FIG. 6B illustrates a top view of the bottom position adjuster in a second lateral position, according to an embodiment.

FIG. 6B illustrates a top view of the bottom position adjuster 114 in a second lateral position 604, according to an embodiment. Some of the features in FIG. 6B are the same or similar to some of the features in FIGS. 1-6A as noted by the same reference numbers, unless expressly described otherwise. Additionally, reference may be made to features shown in any of FIGS. 1-6A and not shown in FIG. 6B. The second lateral position 604 of the top position adjuster 108 relative to the bottom position adjuster 114 may be reflected in the relative position of the protuberances 116 in the channels 118. The top position adjuster 108 may be shifted right relative to the bottom position adjuster 114. The top position adjuster 108 may also be shifted forward relative to the bottom position adjuster 114, reflecting an overbite of the individual 100. The protuberances 116 may shift in the channels 118, which may allow the lower mandible 100e of the individual 100 to shift side to side. However, the protuberances 116 and channels 118 may prevent the lower mandible 100e of the individual 100 from sliding backward or forward relative to the upper mandible 100d. The protuberances 116 may hook into the channels 118 to secure the top position adjuster 108 to the bottom position adjuster 114.

The protuberances 116 and channels 118 may also prevent the top position adjuster 108 from unintentionally coming apart from the bottom position adjuster 114. In another embodiment, the protuberances 116 may be slightly misaligned with the channels 118 and/or openings in the channels 118. By pushing in on the pressing surface 414 of the upper mandible tray 104 and/or the lower mandible tray 110, the user may adjust the position or configuration of the top position adjuster 108 and/or the bottom position adjuster 114. The channels 118 may have a wavy shape. The protuberances 116 may be flexible and may bend to conform to the wavy shape of the channels 118.

Figure 7A:
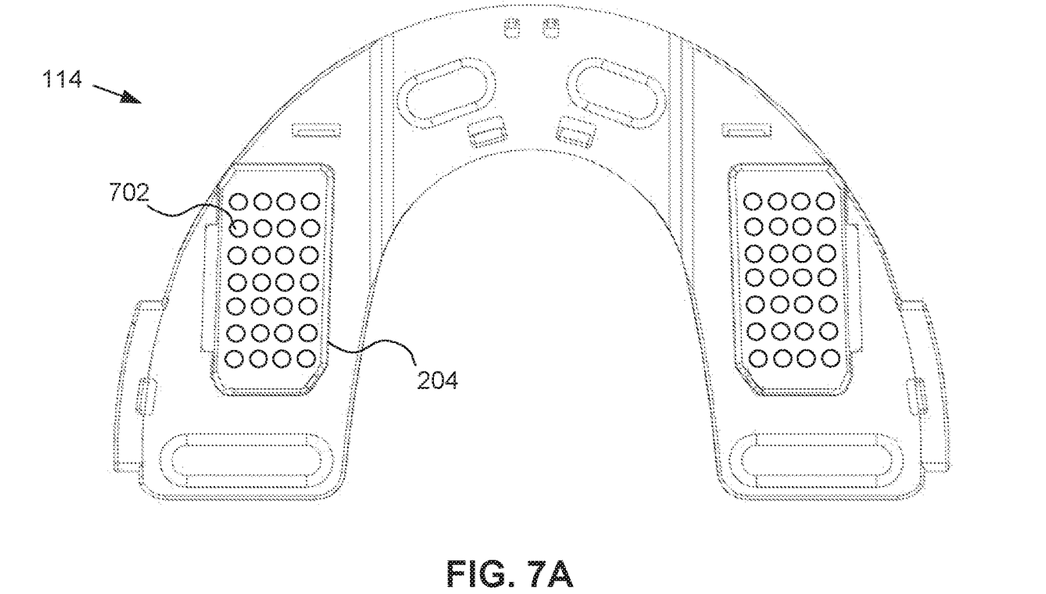
FIG. 7A illustrates a bottom position adjuster with cavities for receiving protuberances from a top position adjuster, according to an embodiment.

FIG. 7A illustrates the bottom position adjuster 114 with cavities 702 for receiving the protuberances 116 from the top position adjuster 108, according to an embodiment. Some of the features in FIG. 7A are the same or similar to some of the features in FIGS. 1-6B as noted by the same reference numbers, unless expressly described otherwise. Additionally, reference may be made to features shown in any of FIGS. 1-6B and not shown in FIG. 7A. In an embodiment, the raised portion 204 of the bottom position adjuster 114 may include the cavities 702. The cavities 702 may receive the protuberances 116 to secure the top position adjuster 108 in place relative to the bottom position adjuster 114.

Figure 7B:
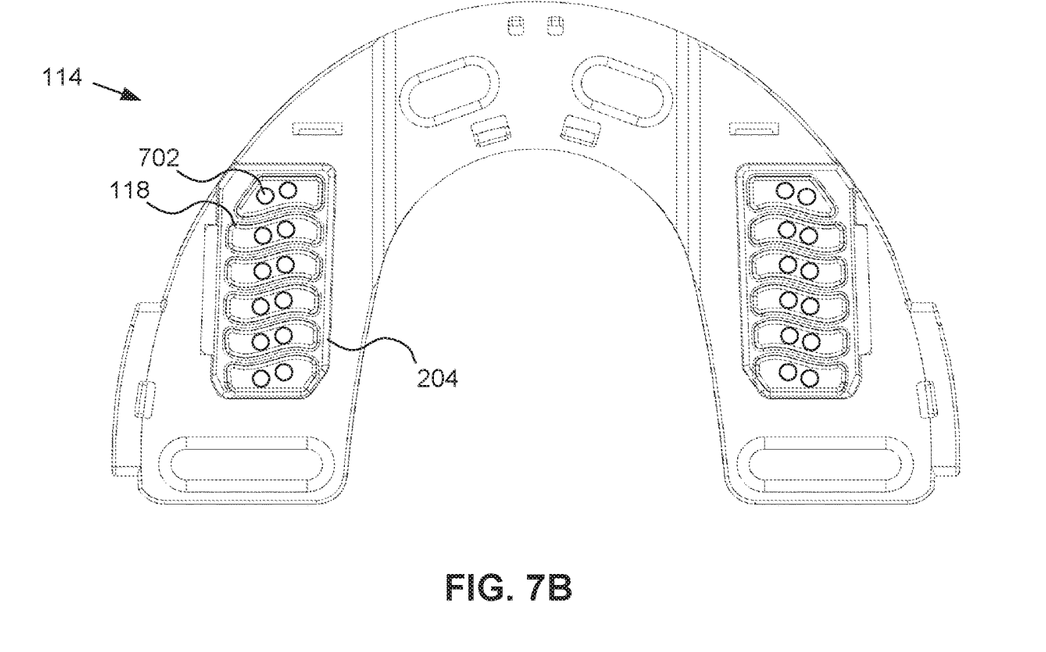
FIG. 7B illustrates the bottom position adjuster with the cavities within channels, according to an embodiment.

FIG. 7B illustrates the bottom position adjuster 114 with the cavities 702 within the channels 118, according to an embodiment. Some of the features in FIG. 7B are the same or similar to some of the features in FIGS. 1-7A as noted by the same reference numbers, unless expressly described otherwise. Additionally, reference may be made to features shown in any of FIGS. 1-7A and not shown in FIG. 7B. In one embodiment, the channels 118 may include the cavities 702 to receive the protuberances 116 of the top position adjuster 108. The channels 118 may extend a partial depth in the raised portion 204, and the cavities 702 may extend to a further depth in the raised portion 204 beyond the depth of the channels 118. The channels 118 may include sloped sides that slope towards the cavities 702. The sloped sides may guide the protuberances 116 towards the cavities 702.

In an embodiment, a channel 118 may include 2 cavities 702. In another embodiment, a channel 118 may include 4 cavities 702. As discussed above, the multiple channels 118 and cavities 702 may allow a user to adjust the upper mandible tray 104 relative to the lower mandible tray 110 by inserting the protuberances 116 into different channels 118 or within different cavities 702 of the same channels 118.

Figure 7C:
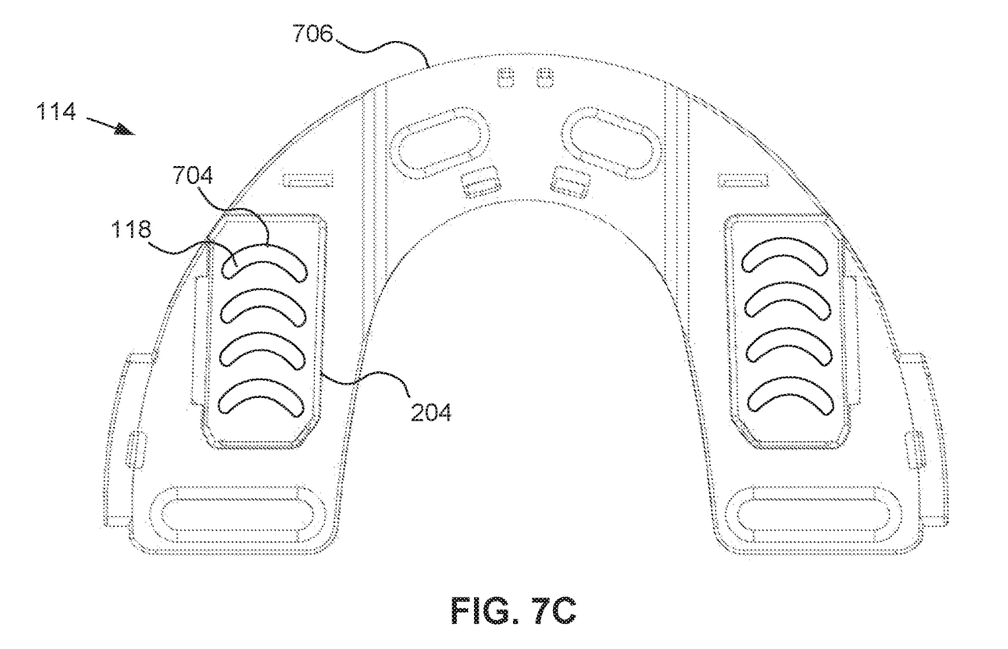
FIG. 7C illustrates the bottom position adjuster with the channels curved backward, according to an embodiment.

FIG. 7C illustrates the bottom position adjuster 114 with the channels 118 curved backward, according to an embodiment. Some of the features in FIG. 7C are the same or similar to some of the features in FIGS. 1-7B as noted by the same reference numbers, unless expressly described otherwise. Additionally, reference may be made to features shown in any of FIGS. 1-7B and not shown in FIG. 7C. In an embodiment, the channel 118 may include a bend. An outside 704 of the bend may face towards a front end 706 of the bottom position adjuster 114. The front end 706 of the bottom position adjuster may be positioned over a bottom incisor of the individual 100 as the individual 100 wears the lower mandible tray 110.

Figure 7D:
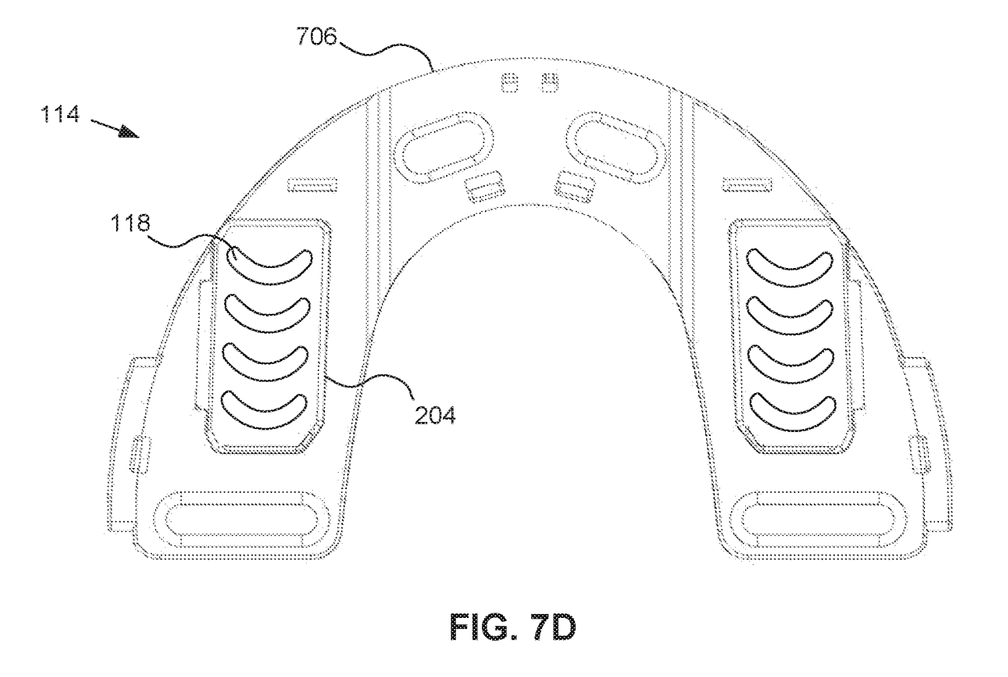
FIG. 7D illustrates the bottom position adjuster with the channels curved forward, according to an embodiment.

FIG. 7D illustrates the bottom position adjuster 114 with the channels 118 curved forwards, according to an embodiment. Some of the features in FIG. 7D are the same or similar to some of the features in FIGS. 1-7C as noted by the same reference numbers, unless expressly described otherwise. Additionally, reference may be made to features shown in any of FIGS. 1-7C and not shown in FIG. 7D. In an embodiment, the channel 118 may be curved towards the front end 706 of the bottom position adjuster 114.

The above description sets forth numerous specific details such as examples of specific apparatuses, components, methods and so forth, in order to provide a good understanding of several implementations. It will be apparent to one skilled in the art, however, that at least some implementations may be practiced without these specific details. In other instances, well-known components or methods are not described in detail or are presented in a simple block diagram format in order to avoid unnecessarily obscuring the present implementations. Thus, the specific details set forth above are merely exemplary. Particular implementations may vary from these exemplary details and still be contemplated to be within the scope of the present implementations.

It is to be understood that the above description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more of such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. An apparatus, comprising:
 a top tray configured to be inserted into a mouth of a user, the top tray comprising:
 an upper teeth channel formed from a thermoplastic material, wherein the upper teeth channel is configured to fit around or conform to two or more upper teeth of the user; and
 a first set of male fasteners protruding from an underside of the top tray;
 a top position adjuster attached to the underside of the top tray, comprising:
 a first set of female fasteners complimentary with the first set of male fasteners, wherein the top tray and the top position adjuster are joined by the first set of male fasteners and the first set of female fasteners to form an upper mandible tray;
 a recess on an underside of the top position adjuster; and
 a set of male position aligners disposed in the recess and extending from the underside of the top position adjuster, wherein:
 the set of male position aligners comprises:
 a first row of aligners comprising:
 a first protrusion comprising a first peg, a first pin, or a first dowel; and
 a second protrusion comprising a second peg, a second pin, or a second dowel; and
 a second row of aligners comprising:
 a third protrusion comprising a third peg, a third pin, or a third dowel; and
 a fourth protrusion comprising a fourth peg, a fourth pin, or a fourth dowel; and
 wherein the recess and the set of male position aligners are positioned on the top position adjuster and are configured to be directly under one or more upper teeth of the user as the user wears the upper mandible tray;
 a bottom tray configured to be inserted into the mouth of the user, comprising:
 a lower teeth channel formed from the thermoplastic material, wherein the lower teeth channel is configured to fit around or conform to two or more lower teeth of the user; and
 a second set of male fasteners protruding from a topside of the bottom tray; and
 a bottom position adjuster attached to the topside of the bottom tray, comprising:
 a second set of female fasteners complimentary with the second set of male fasteners, wherein the bottom tray and the bottom position adjuster are joined by the second set of male fasteners and the second set of female fasteners to form a lower mandible tray;
 a raised portion comprising walls extending from a topside of the bottom position adjuster and defining a set of openings therein, wherein:
 the set of openings is positioned on the bottom position adjuster and is configured to be located directly over one or more lower teeth of the user as the user wears the lower mandible tray; and
 wherein the raised portion including the set of openings is configured to fit into the recess in the top position adjuster and over the set of male position aligners to connect the upper mandible tray and the lower mandible tray to each other;
 the set of openings comprising:
 a first cavity or a first channel configured to receive one of the first row of aligners or the second row of aligners;
 a second cavity or a second channel configured to receive one of the first row of aligners or the second row of aligners; and
 a third cavity or a third channel configured to receive one of the first row of aligners or the second row of aligners, wherein the set of male position aligners and the set of openings are configured to connect to adjust an alignment of the upper mandible tray and the lower mandible tray laterally and longitudinally; and
 wherein, the apparatus is configured so that as the user wears the upper mandible tray and the lower mandible tray, a position of the upper mandible tray relative to a position of the lower mandible tray in the mouth of the user prevents occlusion or obstruction of an airway of the user as the user sleeps.

2. The apparatus of claim 1, wherein:
 the top tray or the bottom tray is a unibody;
 the thermoplastic material comprises a molding temperature less than or equal to 200° F.; and
 the first set of male fasteners retain shape as the upper teeth channel is molded to the upper teeth of the user or the second set of male fasteners retain shape as the lower teeth channel is molded to the lower teeth of the user.

3. The apparatus of claim 1, further comprising: a snap joint formed by a first wall of the set of openings and a second wall of the recess, wherein: the snap joint comprises a hook and a catch; and the snap joint connects the upper mandible tray to the lower mandible tray; and a pressing surface coupled to the hook or the catch, wherein, as the upper mandible tray and the lower mandible tray are connected, pressure on the pressing surface deflects the hook or the catch to disconnect the upper mandible tray and the lower mandible tray from one another.

4. The apparatus of claim 1, wherein:
the top tray comprises a first unibody thermoplastic;
the top position adjuster comprises a first unibody injection-molded plastic;
the bottom tray comprises a second unibody thermoplastic; and
the bottom position adjuster comprises a second unibody injection-molded plastic.

5. The apparatus of claim 1, further comprising a spacer tab extending between the top position adjuster and the bottom position adjuster, wherein: the spacer tab is integrated with the top position adjuster or the bottom position adjuster; the spacer tab is positioned on the top position adjuster or the bottom position adjuster and configured to be positioned between incisors of the user as the user wears the upper mandible tray or the lower mandible tray; and the spacer tab is configured to maintain an open airway between the upper mandible tray and the lower mandible tray as the user wears the upper mandible tray and the lower mandible tray.

6. An apparatus, comprising:
a top tray configured to be inserted into a mouth of a user, the top tray comprising:
an upper teeth channel configured to fit around upper teeth of the user; and
a first set of fastener sides on an underside of the top tray;
a top position adjuster, comprising:
a second set of fastener sides complimentary with the first set of fastener sides, wherein the top tray and the top position adjuster are joined by the first set of fastener sides and the second set of fastener sides to form an upper mandible tray;
a set of position aligners on an underside of the top position adjuster, wherein the set of position aligners comprises:
a first row of aligners comprising:
a first protrusion comprising a first peg, a first pin, or a first dowel; and
a second protrusion comprising a second peg, a second pin, or a second dowel; and
a second row of aligners comprising:
a third protrusion comprising a third peg, a third pin, or a third dowel; and
a fourth protrusion comprising a fourth post, a fourth peg, a fourth pin, or a fourth dowel; and
a bottom tray configured to be inserted into the mouth of the user, the bottom tray comprising:
a lower teeth channel configured to fit around lower teeth of the user; and
a third set of fastener sides on a top side of the bottom tray; and
a bottom position adjuster, comprising:
a fourth set of fastener sides complimentary with the third set of fastener sides, wherein the bottom tray and the bottom position adjuster are joined by the third set of fastener sides and the fourth set of fastener sides to form a lower mandible tray;
a set of openings corresponding to the set of position aligners and positioned on a top side of the bottom position adjuster, the set of openings comprising:
a first cavity or a first channel configured to receive one of the first row of aligners or the second row of aligners;
a second cavity or a second channel configured to receive one of the first row of aligners or the second row of aligners; and
a third cavity or a third channel configured to receive one of the first row of aligners or the second row of aligners, wherein the set of position aligners and the set of openings are configured to connect to adjust an alignment of the upper mandible tray and the lower mandible tray laterally and longitudinally;
wherein, the apparatus is configured so that as the user wears the upper mandible tray and the lower mandible tray, the set of position aligners is positioned to fit into the set of openings to connect the upper mandible tray and the lower mandible tray in a first position; the set of position aligners is positioned to fit into the set of openings to connect the upper mandible tray and the lower mandible tray in a second position that is different from the first position;
wherein the first position and the second position are laterally and longitudinally different; and wherein the upper mandible tray and the lower mandible tray are configured to prevent occlusion or obstruction of an airway of the user.

7. The apparatus of claim 6, wherein: the top tray comprises a first compressible barrier configured to be positioned between the upper teeth and the top position adjuster as the user wears the upper mandible tray; or the bottom tray comprises a second compressible barrier configured to be positioned between the lower teeth and the bottom position adjuster as the user wears the lower mandible tray.

8. The apparatus of claim 6, wherein: the top tray comprises a remoldable polymer, wherein the remoldable polymer retains shape at a temperature up to 110° F. and changes shape at a temperature between 110° F. and 200° F.; the bottom tray comprises the remoldable polymer; the top position adjuster comprises a rigid polymer, wherein the rigid polymer retains shape at temperatures between 110° F. and 200° F.; or the bottom position adjuster comprises the rigid polymer.

9. The apparatus of claim 8, wherein:
the remoldable polymer comprises ethylene-vinyl acetate; or
the rigid polymer comprises polyurethane plastic.

10. The apparatus of claim 6, wherein:
the first set of fastener sides, the second set of fastener sides, the third set of fastener sides and the fourth set of fastener sides each comprise a hook-and-catch snap joint.

11. An apparatus comprising:
a top tray configured to be inserted into a mouth of a user, the top tray comprising:
an upper teeth channel configured to fit around upper teeth of the user; and
a first set of fastener sides on an underside of the top tray;
a top position adjuster, comprising:
a second set of fastener sides complimentary with the first set of fastener sides, wherein the top tray and the top position adjuster are joined by the first set of fastener sides and the second set of fastener sides to form an upper mandible tray;

a set of position aligners on an underside of the top position adjuster, wherein the set of position aligners comprises:
a first row of aligners comprising a first peg and a second peg; and
a second row of aligners comprising a third peg and a fourth peg; and
a bottom tray configured to be inserted into the mouth of the user, the bottom tray comprising:
a lower teeth channel configured to fit around lower teeth of the user; and
a third set of fastener sides on a top side of the bottom tray; and
a bottom position adjuster configured such that a front of the bottom position adjuster is positioned over a bottom incisor of the user as the user wears the lower mandible tray, the bottom position adjuster comprising:
a fourth set of fastener sides complimentary with the third set of fastener sides, wherein the bottom tray and the bottom position adjuster are joined by the third set of fastener sides and the fourth set of fastener sides to form a lower mandible tray;
a set of openings corresponding to the set of position aligners and positioned on a top side of the bottom position adjuster, the set of openings comprising:
a first channel configured to be aligned perpendicularly to a row of bottom teeth of the user and configured to receive one of the first row of aligners or the second row of aligners;
a second channel configured to be aligned perpendicularly to a row of bottom teeth of the user and configured to receive one of the first row of aligners or the second row of aligners; and
a third channel configured to be aligned perpendicularly to a row of bottom teeth of the user and configured to receive one of the first row of aligners or the second row of aligners, wherein the set of position aligners and the set of openings are configured to connect to adjust an alignment of the upper mandible tray and the lower mandible tray laterally and longitudinally;
wherein: the first channel, second channel and third channel is are each curved towards the front of the bottom position adjuster or each comprise a bend, wherein an outside of the bend faces towards the front of the bottom position adjuster;
wherein the apparatus is configured so that as the user wears the upper mandible tray and the lower mandible tray, the set of position aligners is positioned to fit into the set of openings to connect the upper mandible tray and the lower mandible tray in a first position; the set of position aligners is positioned to fit into the set of openings to connect the upper mandible tray and the lower mandible tray in a second position that is different from the first position;
wherein the first position and the second position are laterally and longitudinally different; and wherein the upper mandible tray and the lower mandible tray are configured to prevent occlusion or obstruction of an airway of the user.

* * * * *